United States Patent [19]

Sakowski

[11] Patent Number: 4,590,939

[45] Date of Patent: May 27, 1986

[54] METHOD OF RELIEF OF PAIN BASED ON THE USE OF A NON-INVASIVE PRESSURE-APPLICATION DEVICE WHICH PRODUCES A HIGHLY-LOCALIZED SELF-INDUCED MASSAGE

[76] Inventor: Carol G. Sakowski, Rte. 1, Box 50, Barneveld, Wis. 53507

[21] Appl. No.: 637,744

[22] Filed: Aug. 6, 1984

Related U.S. Application Data

[63] Continuation of Ser. No. 463,297, Feb. 2, 1983, abandoned.

[51] Int. Cl.⁴ ............................................. A61B 17/34
[52] U.S. Cl. .................................................. 128/329 A
[58] Field of Search ...................... 128/165, 327, 329

[56] References Cited

U.S. PATENT DOCUMENTS 4,182,338  1/1980  Stanulis ............................... 128/329
4,479,495  10/1984  Isaacson ............................. 128/327

Primary Examiner—John D. Yasko
Assistant Examiner—Karen L. Kaechele
Attorney, Agent, or Firm—M. Paul Hendrickson

[57] ABSTRACT

Disclosed is a method for relief of pain in mammals based on the use of a pressure-application device which is applied to any of a number of points selected and located according to the principles and practices of traditional acupressure and/or acupuncture therapy practice, which produces a highly-localized self-induced massage of the acupressured point which results in relief of pain in an area of the body not necessarily at the point acupressured, which relief lasts for an extended period of time past the time at which the device is removed according to the method of the invention.

6 Claims, 13 Drawing Figures

METHOD OF RELIEF OF PAIN BASED ON THE USE OF A NON-INVASIVE PRESSURE-APPLICATION DEVICE WHICH PRODUCES A HIGHLY-LOCALIZED SELF-INDUCED MASSAGE

This application is a continuation of my co-pending application, Ser. No. 463,297, and title "A Method of Relief of Pain Based on the Use of a Non-Invasive Pressure-Application Device Which Produces a Highly-Localized Self-Induced Massage", and Filing Date 03/83.

BACKGROUND OF THE INVENTION

This invention relates to the relief of pain by the application of pressure to selected points on the body.

There has been a small number of devices previously patented in the field of acupressure and acupuncture therapy for a variety of purposes, among them treatment of a variety of physiologic abnormalities, but these devices have been designed and intended for use in very specific ways. For example, for use in such treatment by application of a pressure-application device of specific design such that it would be applied only to the ear or to the finger of human beings; or for use in stopping the flow of blood at a sampling-needle puncture site in kidney-dialysis patients so that it did not present a hazard to their successful treatment by that modality. Refer to U.S. Pat. Nos. 4,122,852, 4,319,574, and 4,182,338 and to the patents to which they refer, respectively, for further information on the subject.

This invention relates to a method of relief of pain by the use of a device which presses on any of a number of points at a variety of locations on the body which are commonly used for relief of pain in acupuncture and/or acupressure therapy practice and which acts to produce a highly-localized self-induced massage which brings relief of pain at some point in the body not necessarily at the point being treated.

Acupuncture therapy for the relief of pain has been practiced by the Chinese for some 2,000 years with a good safety record and an excellent success record, even when practiced by illerate lay personnel. However, acupuncture is an invasive technique, and one which thus leaves the recipient open to introduction of pathogenic organisms. Thus, despite its well-documented success as a treatment for a variety of physiologic conditions, among them pain, it is not completely suitable for use by the lay population.

Acupressure therapy for the relief of pain has been practiced by the Chinese for some 4,000 years, however, with an excellent safety record and an equally-good success record. And it has the advantage of being a non-invasive technique, thus eliminating the possibility of introduction of pathogenic organisms into the recipient. Acupressure therapy, then, being a form of highly-localized massage, is emminently more suitable for use by lay personnel for the relief of pain.

In a number of species of mammals, a number of points commonly used in both acupuncture and in acupressure therapy are relatively close to the surface of the body, and thus are easily worked on to effect some measure of relief from pain from any of a variety of causes; for example, arthritises.

In equines, for example, such pain can render an animal very difficult to work on, for both the veterinarian and the farrier. Methods traditionally used to make the animal stand quietly have been the use of tranquilizing drugs, and/or the use of a device commonly referred to as a "twtich", which provides considerable pain in either the nose of ear area which focusses the animal's attention on the twitched area and renders the animal immobile to some extent through its desire to avoid further intensifying the pain from the twitch.

Such methods are either decidedly inhumane or have some degree of danger associated with them from possible negative reaction of the animal to the subsituted pain or from anaphylactic shock or from the introduction of pathogenic organisms when the tranquilizing drug is administered (since such administration is usually done by injection in animals).

In humans, relief of pain and subsequent restoration of even partial freedom of movement (regardless of the cause of the pain) is the paramount consideration. Twitching is not done in humans, but administration of tranquilizing and/or pain-blocking drugs is, and it has some degree of risk associated with it, both from the possibility of physiologic reaction and, when administration is done either by injection or intravenous tube, from the possibility of introduction of pathogenic organisms.

In traditional acupuncture therapy, a skilled technician has had to remain in attendance, both in human and in non-human practice. Additionally, it has been known for a long time that repeated and extended use of points will result eventually in what is referred to as "acupuncture point fatigue", after which time such fatigued points respond considerably less well to further acupuncture therapy. Refer to U.S. Pat. Nos. 4,122,852 and 4,319,474 and to the patents which they cite as references for further information on this subject. Due to the need for complete relaxation of the muscles of the recipient at the time of needle placement, self-therapy by acupuncture has not been considered very feasible, not to mention the previously-referred-to potential for infection.

In traditional acupressure therapy, a technician has had to remain in attendance in order to provide the needed pressure(s). In humans, this is not always necessary, but the need to remain in a contorted or cramped position made self-therapy difficult or uncomfortable. In veterinary situations, the need for such an extra person is often difficult to fulfill. Additionally, the technician would have to remain in a cramped position for an extended period of time in order to work on the desired points in certain instances. Too, the number of points which can be simultaneously acupressured is limited to how many the technician can manipulate with two hands, both in human and in veterinary medicine. In humans, for example, well over 349 points, located all over the body. are known and used, many of simultaneously. Refer to the books "THE HEALING BENEFITS OF ACUPRESSURE" by F. M. Houston, D.C., and "ACUPUNCTURE MANUAL, A Western Approach" by Luke S. W. Chu, M.D., Samuel D. J. Yeh, M.D., and Denise D. Wood for further information on the subject. In animals, well over 100 points are known to exist for the equine alone, and similar points exist for other animals. Refer to "VETERINARY ACUPUNCTURE" by Alan M. Klide, D.V.M. and Shiu H. Kung, Ph.D. for further information on the subject.

In non-human situations, the simple presence of an extra body can make working around the animal more difficult for the veterinarian and/or the farrier, due to the size of the animal and the fact that conditions in barns are often somewhat restricted when comparing the size of the animal and the space in which it is kept; e.g., stalls and aisles.

SUMMARY OF THE INVENTION

This method provides for the use of a pressure-application device, according to the method of the invention, which device is secured by straps to provide the needed pressure on the points recommended by the traditional disciplines of either acupressure or acupuncture to produce a highly-localized self-induced massage which relieves pain in some area of the body not necessarily at the point acupressured and which does not require the constant attention of a technician, nor does it require either the technician or the user to remain in a contorted, cramped, or uncomfortable position for an extended period of time, and which relief of pain lasts for an extended period of time past the time at which the device is removed. This is true whether the therapy is done on another person, an animal, or is self-practiced. The method, through the use of the device, produces a highly-localized, self-induced massage of the point on which it presses, and causes relief of pain in an area not necessarily at the acupressured point. Any person can be quickly and easily trained in the method and the use of the associated device, and thus one individual can apply the method and the associated device and go on to perform other tasks during the time the method and the ass ciated device are applied. Complete physical relaxation is not essential as it is in acupuncture therapy and, in fact, mild gentle activity often intensifies the massage and aids in the relief of pain. In traditional acupressure therapy, no maximum time limits are normally given beyond which any negative or destructive effects might occur, therefore any danger from leaving the device on for too long a period of time does not exist.

The securing strap or straps are elastomeric in nature, and are only pulled snug (not tight), thus normal blood flow is not impeded and this device does not act in any way as a tourniquet, nor does it impede any normal physiologic function other than the flow of pain impulses. Little, if any, sub-surface tissue damage occurs, and never any of a serious or permanent nature, due to the design of the device and the method by which it is used.

Another objective of this invention is to produce a device which is as comfortable as possible for the wearer for relatively extended periods of time, and on a repeat basis, while effectively pressure-massaging the selected point, and which device will not puncture the skin of the mannal on which it is used.

The present invention will be more fully understood by referring to the accompanying drawings, in which.

DETAILED DESCRIPTION OF THE INVENTION

Figure 1:
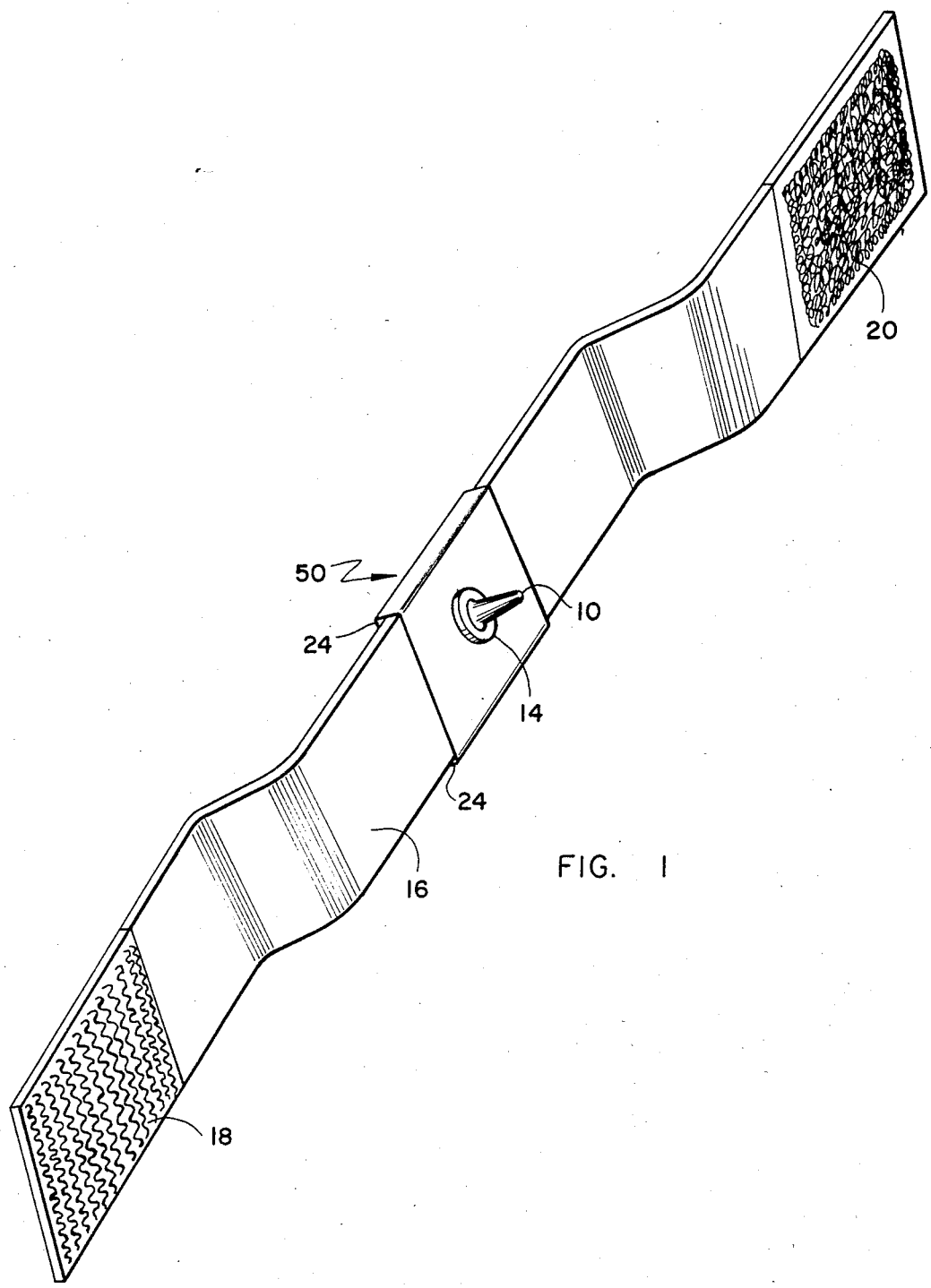
FIG. 1 is a pictorial view of a disclosed embodiment of a pressure-application device according to the present invention.
Figure 2:
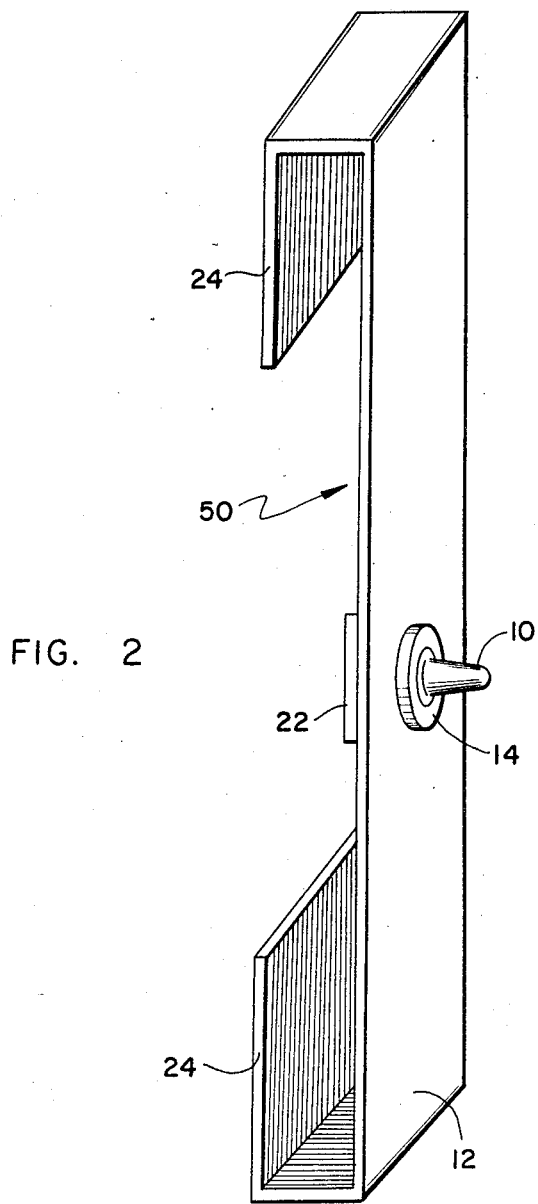
FIG. 2 is a plan view of an embodiment of the pressure-application device according to the present invention.
Figure 3:
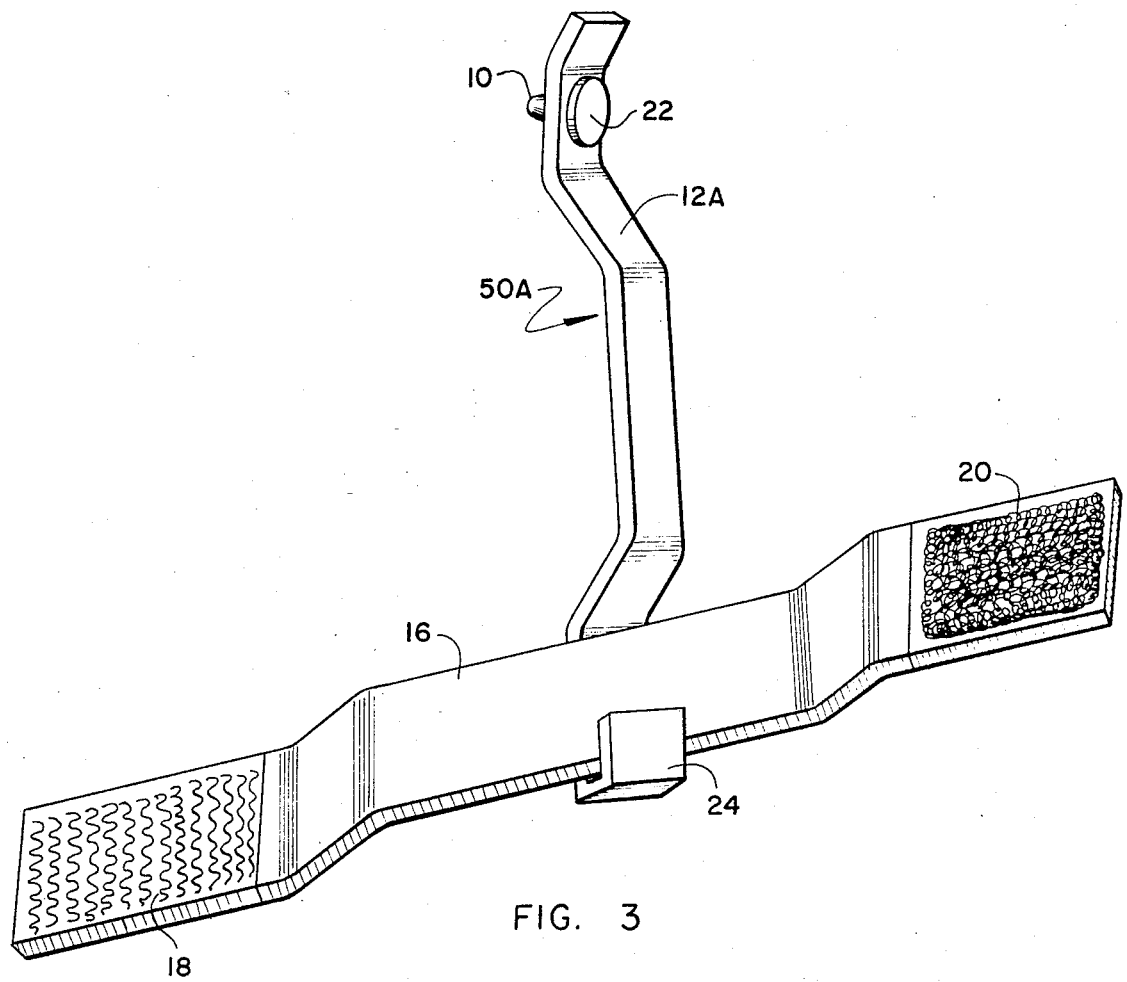
FIG. 3 is a pictorial view of another embodiment of the pressure-application device according to the present invention, this particular embodiment being made specifically to enable the technician to place the active part of the device on the precise spot desired, which is not otherwise reachable with the embodiment shown in FIG. 1 (refer to FIGS. 8 and 9 for further further clarification)
Figure 4:
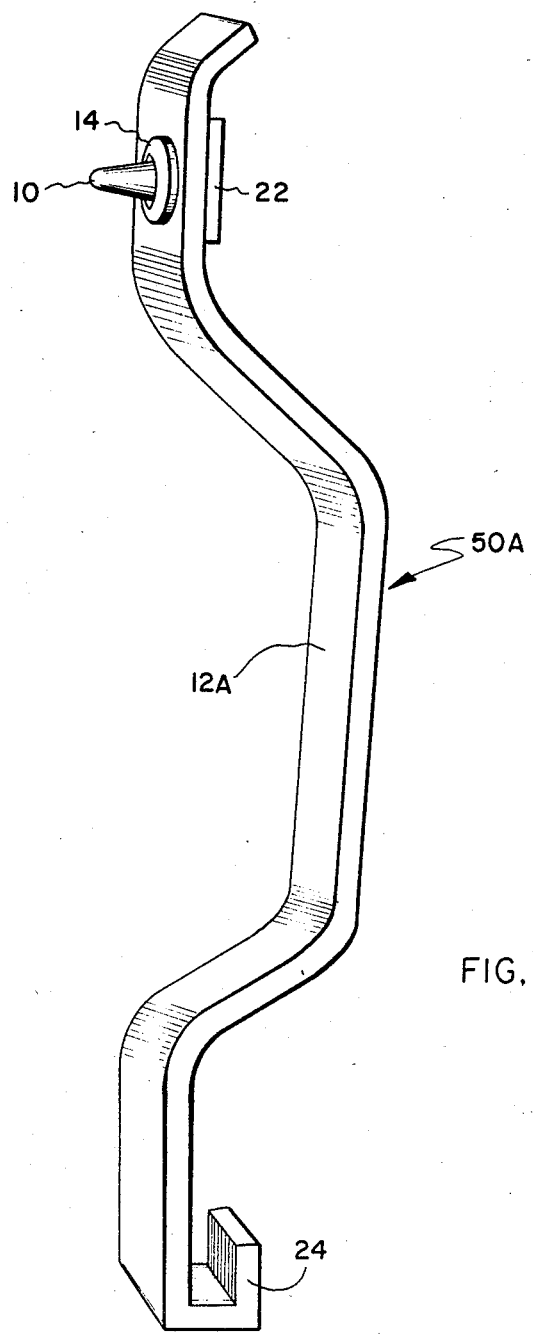
FIG. 4 is a plan view of the embodiment shown in FIG. 3.
Figure 5:
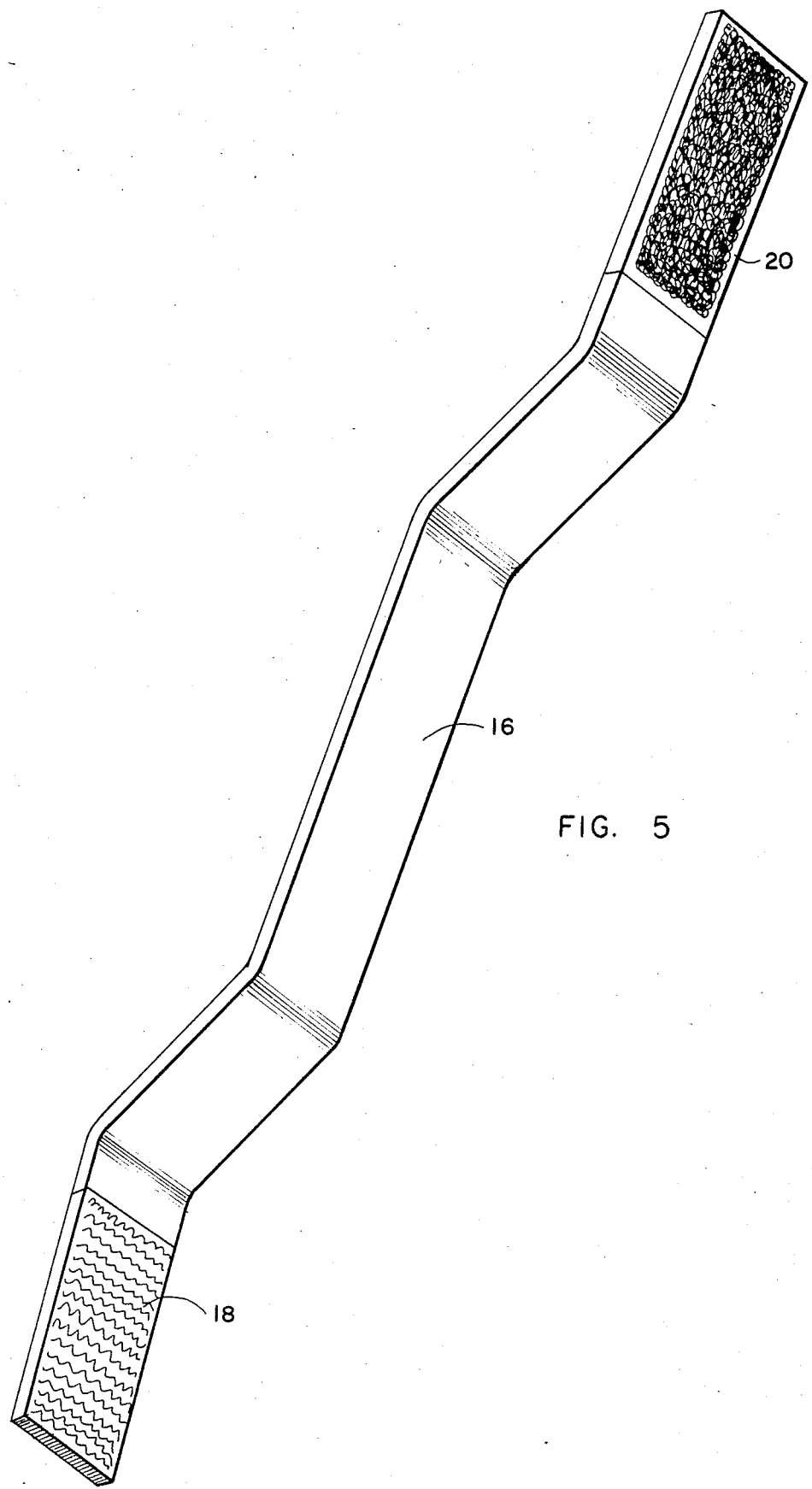
FIG. 5 is a plan view of a disclosed embodiment of the securing strap.
Figure 6:
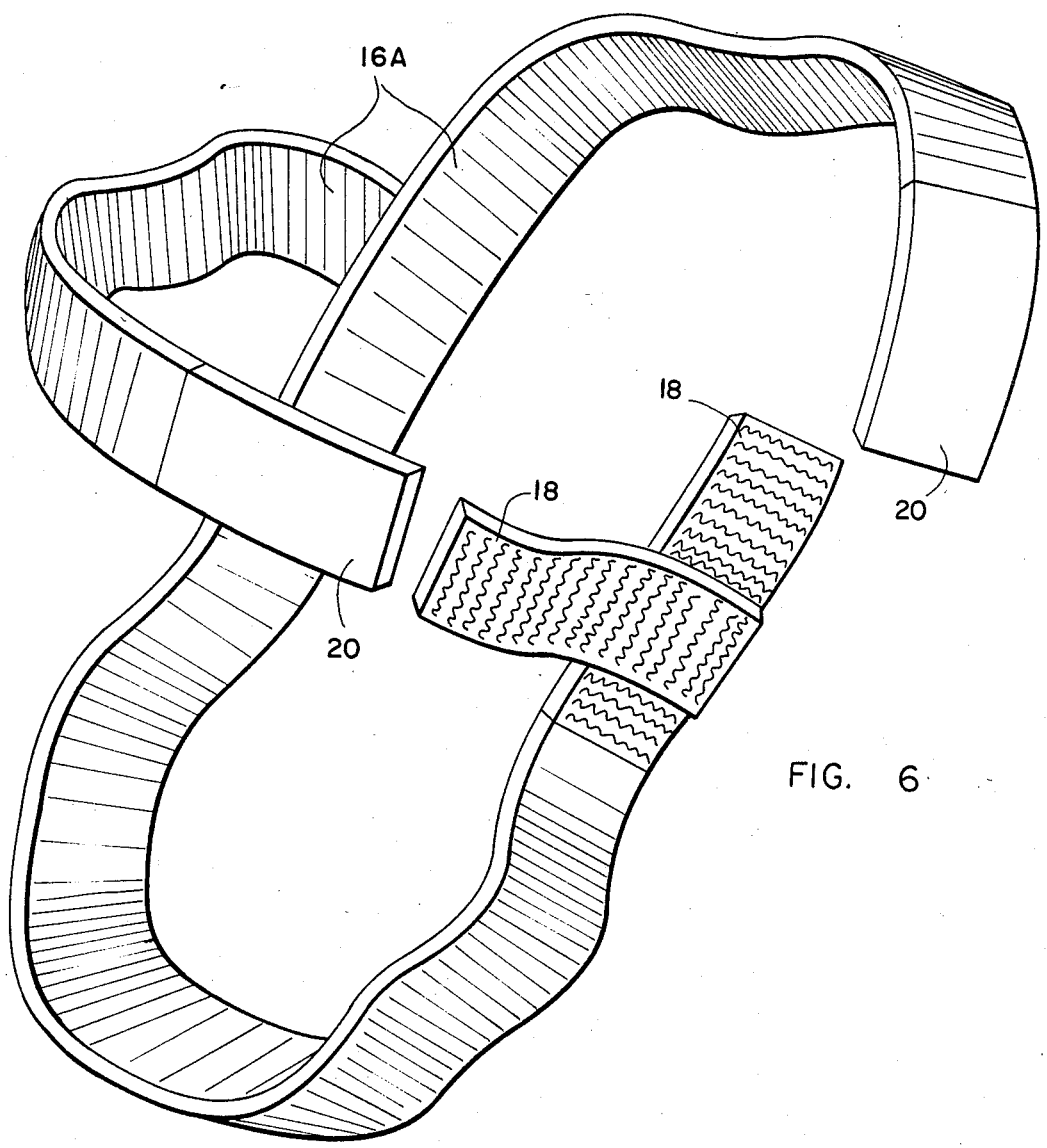
FIG. 6 is a plan view of another embodiment of the securing strap, this one of the strap as it is needed for use as shown in FIGS. 10 and 11, and on other areas such as the hock in equines and other 4-legged animals and/or the heel and/or ankle area in humans.
Figure 7:
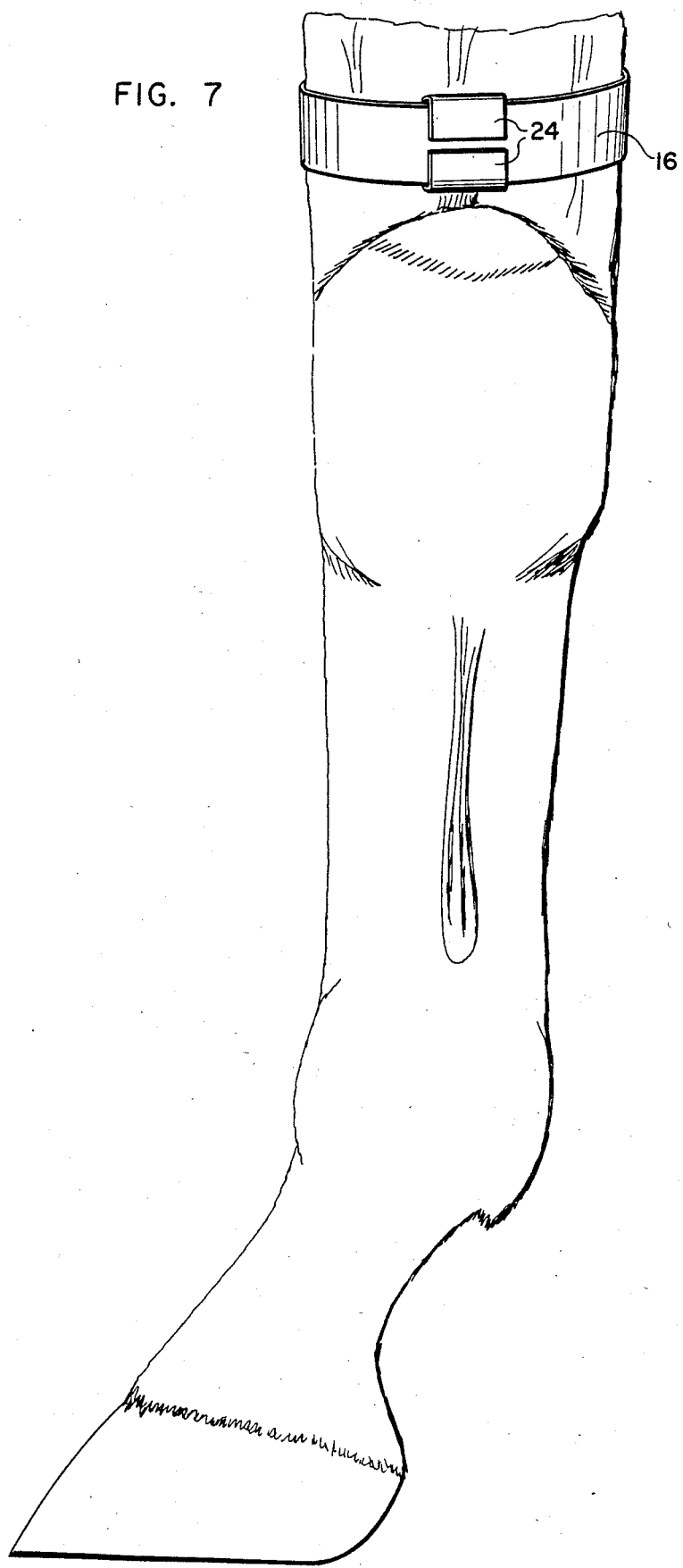
FIG. 7 is a pictorial view of a typical use of the invention for relief of pain in the front legs and shoulders of an equine.
Figure 8:
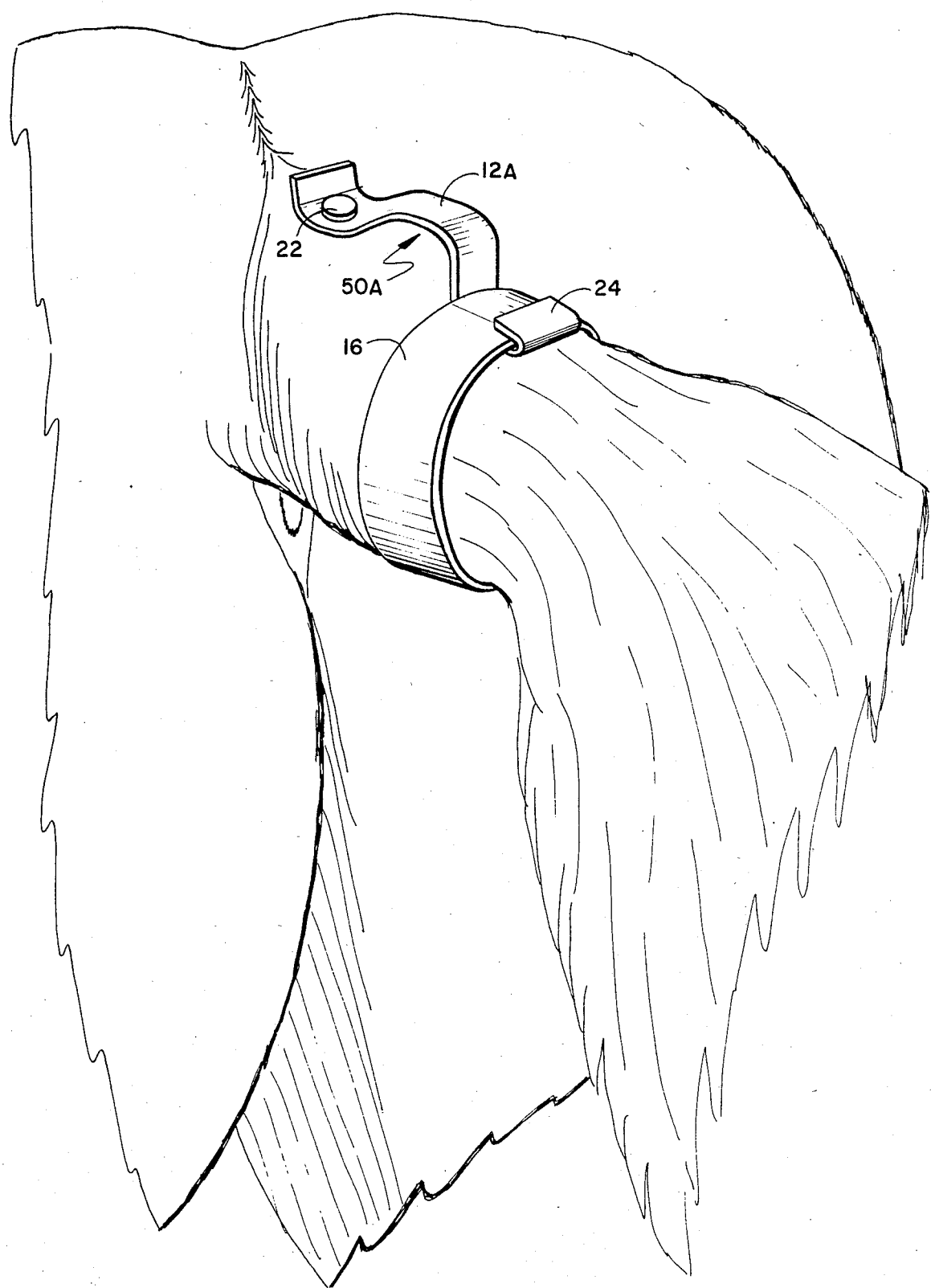
FIG. 8 is a pictorial view of another typical use of the invention for relief of pain in the hindquarters and hind legs of an equine.
Figure 9:
FIG. 9 is a side-elevational pictorial view of a typical use of the invention for relief of pain in the hindquarters and hind legs of an equine.
Figure 10:
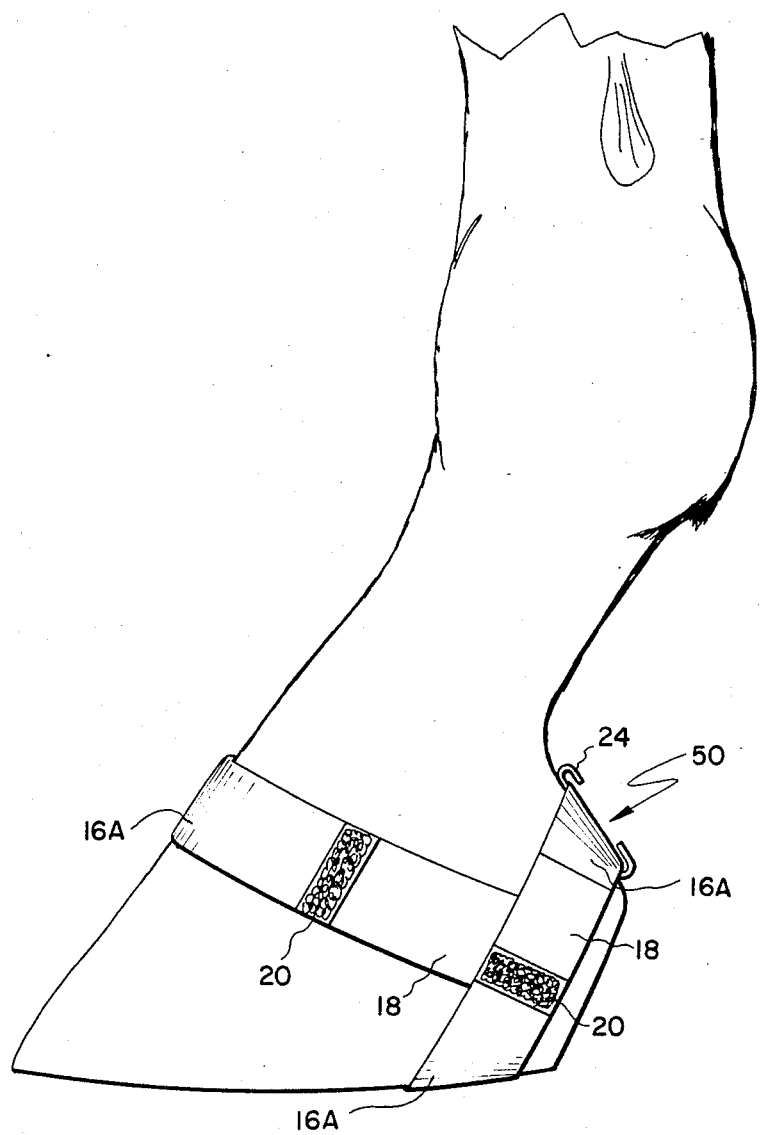
FIG. 10 is a side-elevational pictorial view of a typical use of the invention for relief of pain from laminitis in the quine.
Figure 11:
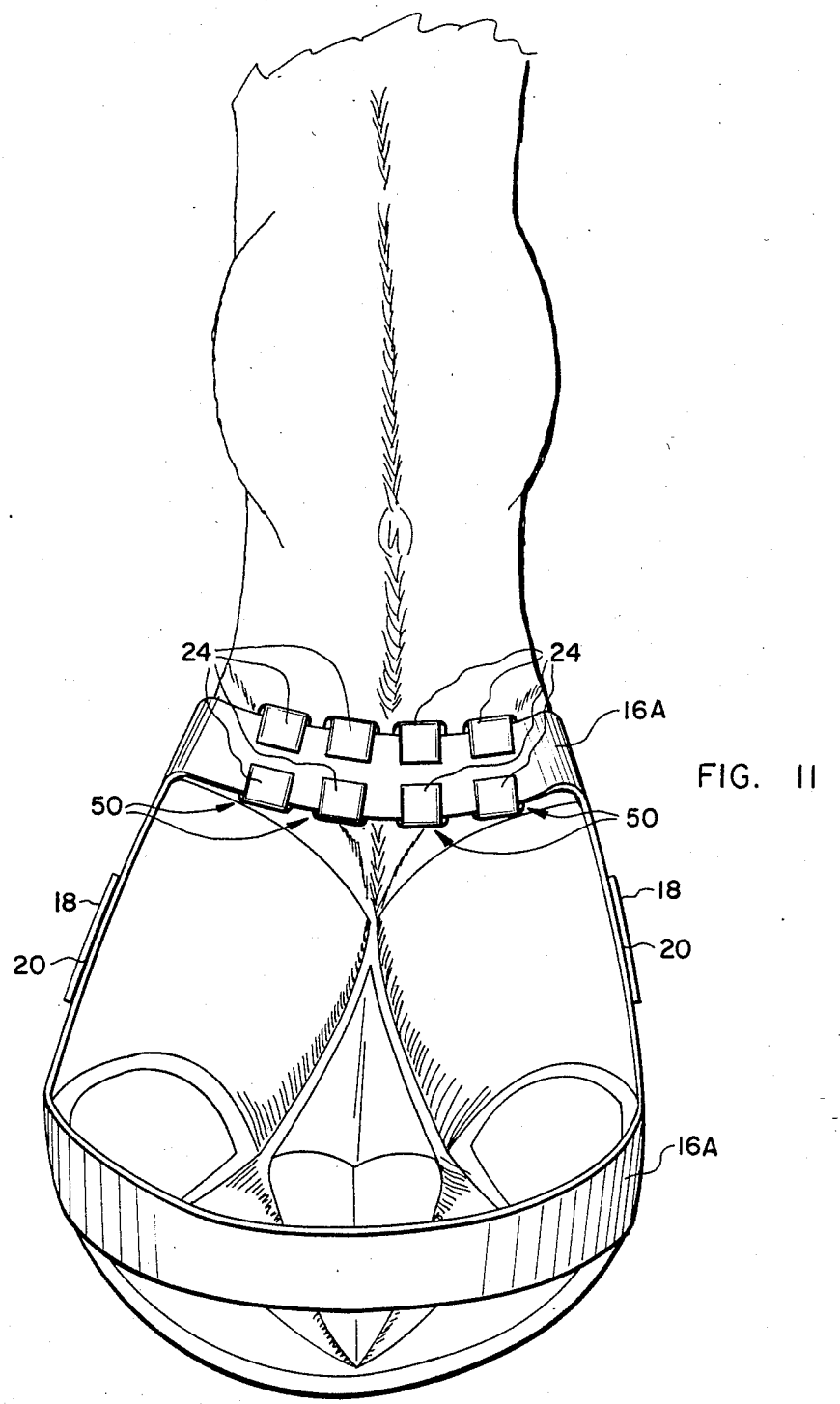
FIG. 11 is a posterio-ventral view of a typical use of the invention for relief of pain from laminitis in the equine.
Figure 12:
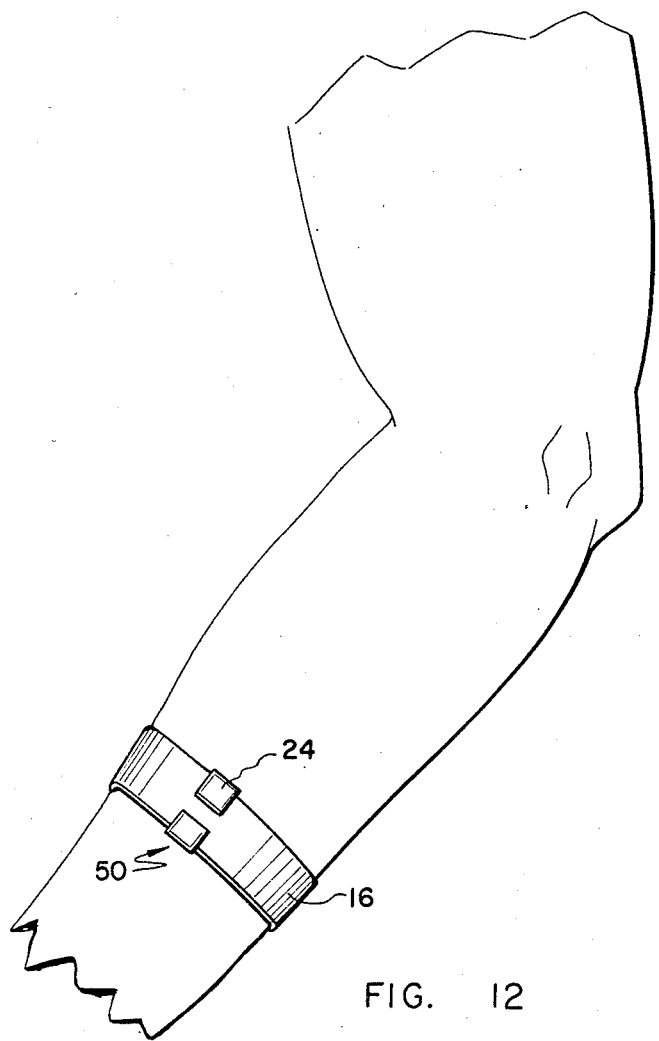
FIG. 12 is a pictorial view showing a typical use of the invention for relief of pain in the arm and shoulder areas in humans.
Figure 13:
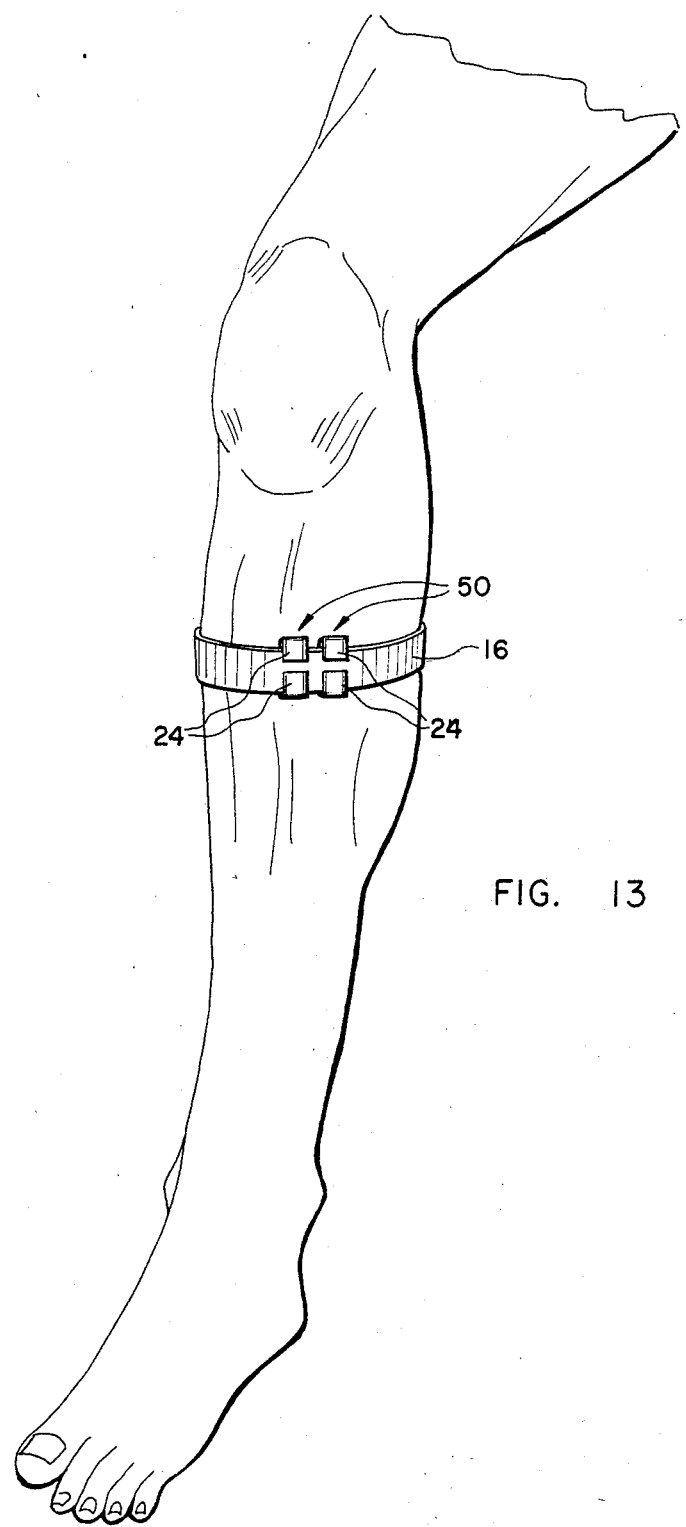
FIG. 13 is a pictorial view showing a typical use of the invention for relief of pain in the feet, legs, and hips of humans.

Referring now specifically to the accompanying drawings wherein like reference numbers designate similar parts throughout the various views shown in FIGS. 1–13, it will be seen that there is a pressure-application device 50 consisting of a supporting surface having an attaching surface and means 12 and 12A, which holds and supports a projection having a rounded blunt body-contacting end 10, which projection is held in place by a ring 14, which device 50 is held in place by an elastomeric securing strap or straps 16 and/or 16A, which are equipped with fasteners 18 and 20, which provide means for securing the pressure-application device or devices over the selected point or points by wrapping the securing strap or straps around the recipient's body member or members and which also act to provide the needed pressure at the same time, as shown in FIGS. 7–13. The part 22 is the base of the projection 10, according to the present invention, and aids in mounting 10 to the body-contacting surface 12 or 12A.

The pressure-application device 50 consists of a flat or gently-curved body having a skin- or body-contacting surface 12 or 12A and one or two attaching surfaces 24. Held by the skin- or body-contacting surface 12 or 12A is a pressure-applicator 10, having a rounded blunt skin- or body-contacting end. The pressure-applicator 10 is generally a truncated cone having a rounded blunt skin- or body-contacting end, occupying less than the total areas of the skin- or body-contacting surface 12 or 12A, and which extends generally perpendicularly outward from the skin- or body-contacting surface 12 or 12A, the base of which 22 aids in mounting 10 to 12 or 12A.

One or both ends of the skin- or body-contacting surface 12 or 12A are formed into attaching structure 24 which enable the pressure-application device 50 to be connected to the securing strap or straps. The attaching structure is formed so that the pressure-application device 50 may be slid along the elastomeric strap or the fasteners 18 or 20 to precisely contact the selected point to be acupressured, while holding the device 50 between the body and the strap.

The pressure-application device 50 may or may not be formed precisely as shown and may or may not be formed from one piece or material, entirely or in any of its parts.

FIGS. 7-13 illustrate typical uses of the invention. The pressure-application device 50 may be used in one of two ways. After determining the site of the pain and the proper point or points to use to obtain relief from this pain, the pressure-application device 50 is either attached to the elastomeric "Velcro"-equipped securing strap 16 or 16A and is then placed over the selected point or points, the securing strap or straps 16 or 16A are wrapped around the body member or members and the fasteners 18 and 20 are belayed and married so as to enable the securing strap or straps to provide the required amount of pressure; or, the securing strap or straps 16 or 16A are wrapped around the body members, the "Velcro" fasteners 18 and 20 are belayed and married so as to provide the estimated tension needed to provide the required pressure when the pressure-application device 50 is slipped between the securing strap or straps 16 or 16A and the body member and has been precisely positioned. In the second case, the tension provided by the securing strap or straps 16 or 16A is then adjusted if necessary to provide the proper amount of pressure on the selected point or points. In either case, when the securing strap or straps 16 or 16A are adjusted to provide the required tension and thus pressure on the point or points, they are only pulled snug, never tight, therefore the pressure-application device 50 and the securing strap or straps 16 or 16A do not act as a tourniquet and do not impede the subsurface flow of blood, nor does either the pressure-application device 50 or the securing strap or straps 16 or 16A i impede any other normal physiological function, nor do they cause any subsurface tissue damage of a serious or permanent nature.

The ability of the pressure-application device 50 to provide relief from pain according to the method of the invention without restricting the sub-surface flow of blood or without restricting any other normal physiological function is due to the method by which it is used as well as by the shoulder effect of both the ring 14 and the skin- or body-contacting surface 12 or 12A. The rounded blunt skin- or body-contacting surface 10 is mounted to the skin or body-contacting surface 12 or 12A such that the pressure applied by the rounded blunt-ended projection 10 accounts for only a portion of the total area of the skin- or body-contacting surface 12 or 12A. In use, the skin- or body-contacting surface 12 or 12A and the ring 14 provide shoulders, in essence, which effectively limits the degree of indentation produced by the rounded blunt-ended projection 10 beyond the area of the body which is not contacted by providing a large area over which to distribute the total force exerted by the pressure-application device 50. In this way, a tourniquet effect is not produced.

It will be readily seen from the drawings that the position of the pressure-application device and the securing strap or straps may be varied by one skilled in the art in order to apply the required amount of tension and pressure to the selected point or points in order to effect the desired result. Thus, it is obvious that the present invention is susceptible to change and modification without departing from the principles of it, and thus it is to be understood that this invention is not limited to the precise arrangement and/or construction of the parts of it shown herein in using this invention in practice, except as claimed.

What is claimed is:

1. The method of applying acupressure therapy to a mammal without necessitating an attendant to manually maintain the positioning of the acupressure device at the acupressure point, said method comprising:
   A. providing an acupressure apparatus comprised of a supporting base member of sufficient surface area to engage the body surface of the mammal, an acupressure projecting member which extends outwardly from said base member to provide acupressure at the acupressure point with said projecting member and said base member cooperatively providing means to limit the amount of acupressure applied to the acupressure point by said acupressure projecting member, at least one elastomeric strap of sufficient length and elasticity to permit the acupressure apparatus to encompass a portion of the body of the mammal at the acupressure point, and means for adjusting and securing said elastomeric strap about the encompassed portion of the mammal while said elastomeric strap is maintained under elastomeric tension,
   B. encompassing the apparatus about the portion of the body of the mammal at the desired acupressure site,
   C. applying acupressure therapy to the acupressure point by adjusting and securing the elastomeric strap to an elastomeric tension sufficient to permit the acupressure projecting member to apply acupressure therapy at the acupressure point,
   D. maintaining the acupressure upon said projecting member at the acupressure point by said apparatus, and
   E. removing the acupressure apparatus from said mammal upon completion of the acupressure therapy.

2. The method according to claim 1 wherein the acupressure apparatus is provided with means for slidably positioning the acupressure member while said elastomeric strap is maintained under sufficient elastomeric tension to permit the application of acupressure to the acupressure point, said method including the additional steps of adjusting and securing the encompassing elastomeric strap to a elastomeric tension to permit the appartus to apply acupressure to the acupressure point and thereafter positioning the acupressure projecting member at the desired acupressure point.

3. The method according to claim 1 wherein the means for adjusting and securing said elastomeric strap comprises a first strap member containing a nap fastening portion and a second strap containing hook fastenig portion, with said method including the steps of adjusting and securing the elastomeric strap by tightening the first and second strap to a sufficient elastomeric tension to permit the apparatus to apply acupressure therapy to the mammal, engaging and securing the hook fastening portion to the nap fastening portion so as to secure and maintain said first and second strap at an elastomeric tension sufficient to permit the application of the acupressure upon said projecting member at the acupressure point.

4. The method according to claim 1 wherein the acupressure apparatus is maintained at a sufficient pressure to provide acupressure therapy without restricting the sub-surface flow of blood in the mammal.

5. The method according to claim 1 wherein the means for adjusting and securing said elastomeric strap of said apparatus comprises a first strap portion and a second strap portion respectively adapted to wrap around the mammal in opposite directions with the combination of said first strap portion and said second strap portion providing means for encompassing a portion of the body of the mammal at the acupressure site and applying sufficient elastomeric tension for the acupressure therapy to said mammal, said method including the additional steps of wrapping said first strap portion and said second strap portion about the mammal in opposite directions at the acupressure site, tightening said first strap portion and said second strap portion to a sufficient elastomeric tension to permit the application of acupressure therapy upon the acupressure point, and securing said first strap portion to said second strap position while maintaining sufficient tension to apply acupressure therapy at the acupressure point of said mammal.

6. The method according to claim 5 wherein the supporting base member in combination with the acupressure projecting member is provided with means of positioning and securing the projecting member at the acupressure point while maintaining the secured first strap portion and said secured second strap portion under elastomeric tension, said method including the additional step of positioning the projecting member at the acupressure point while maintaining the first strap portion and the second strap portion under sufficient elastomeric tension to permit the positioned projecting member to apply acupressure therapy to the acupressure point.

* * * * *